United States Patent [19]

Denis

[11] Patent Number: 5,516,441
[45] Date of Patent: May 14, 1996

[54] SULFUR-COUPLED SALIGENIN SALTS

[75] Inventor: Richard A. Denis, Auburn Township, Ohio

[73] Assignee: The Lubrizol Corporation, Wickliffe, Ohio

[21] Appl. No.: 233,666

[22] Filed: Apr. 26, 1994

[51] Int. Cl.$^6$ ............................................. C10M 129/10
[52] U.S. Cl. ................ 252/42.7; 252/48.2; 252/49.6; 568/716; 568/6; 568/25; 568/727
[58] Field of Search .................. 252/42.7, 48.2, 252/49.6; 568/6, 25, 716, 727

[56] References Cited

U.S. PATENT DOCUMENTS

| | | | |
|---|---|---|---|
| 2,647,873 | 8/1953 | Matthews et al. | 252/42.7 |
| 2,736,701 | 2/1956 | Neff | 252/32.7 |
| 3,425,989 | 2/1969 | Shepard et al. | 260/55 |
| 3,793,201 | 2/1974 | Karn | 252/33.4 |
| 3,951,830 | 4/1976 | Karn | 252/42.7 |
| 3,992,308 | 11/1976 | Malec et al. | 252/48.2 |
| 4,021,419 | 5/1977 | Karn | 252/42.7 |
| 4,147,643 | 4/1979 | Pindar et al. | 252/52 |
| 4,769,501 | 9/1988 | Iwahara | 568/799 |
| 4,778,612 | 10/1988 | Wirth et al. | 252/42.7 |
| 5,240,624 | 8/1993 | Koch | 252/49.6 |
| 5,326,488 | 7/1994 | Minokami et al. | 252/49.6 |
| 5,376,290 | 12/1994 | Meier et al. | 252/48.2 |

FOREIGN PATENT DOCUMENTS

| | | |
|---|---|---|
| 58-180469 | 1/1984 | Japan . |
| 1014655 | 12/1965 | United Kingdom . |
| 596150 | 1/1984 | United Kingdom . |

*Primary Examiner*—Jacqueline V. Howard
*Attorney, Agent, or Firm*—David M. Shold; Frederick D. Hunter, Sr.

[57] ABSTRACT

A metal salt or boron compound of a hydrocarbyl-substituted aromatic hydroxy compound having at least two hydroxy-substituted aromatic rings bridged by sulfur, where at least one aromatic ring bears a substituent ortho to a hydroxy group, provides a useful lubricant additive. The substituent on the aromatic ring is an α-hydroxy aliphatic hydrocarbyl group or a —C(O)R$^2$ group, where R$^2$ is hydrogen or aliphatic hydrocarbyl. Preferred salts are magnesium.

29 Claims, No Drawings

SULFUR-COUPLED SALIGENIN SALTS

BACKGROUND OF THE INVENTION

The present invention relates to metal salts of certain hydroxyaromatic compounds and methods of their preparation.

Metal salts of organic acidic materials have found extensive use in lubricant and fuel applications. A particularly prominence has been obtained by overbased salts, that is, salts which have been formed with an excess of base (often present as the carbonate). These materials serve as detergents in motor oil lubricants. Neutral and overbased salts have been prepared with a variety of metals and a variety of anions, including carboxylate, sulfonate, phenate, and others. However, formation of metal phenates has generally proved difficult, particularly with certain metals such as magnesium. In difficult cases only partial neutralization is possible without taking extreme measures. The present invention provides certain phenolic salts which are easy to prepare as substantially fully neutralized or even overbased materials.

U.S. Pat. No. 2,647,873, Matthews et al, Aug.4, 1953, discloses a lubricating composition containing a reaction product of an aromatic compound containing a polar radical, represented by the general formula $R_m$—Ar—$R'_m$—$(X)_q$, and an aldehyde such as formaldehyde, simultaneously reacted with a basic metallic compound such as calcium hydroxide. The reaction is generally carried out at a temperature ranging from about 50° C. to about 150° C. The product is subjected to a heat treatment.

U.S. Pat. No. 2,736,701, Neff, Feb. 28, 1956, discloses a lubricating oil composition which contains an oil-soluble complex obtained by heating an oil solution of a metal salt of a hydrocarbon substituted phenol-aldehyde condensation product and adding a basic metal inorganic compound. An example is the calcium salt of the tert-octylphenol-formaldehyde resin.

U.S. Pat. No. 3,425,989, Shepard et al., Feb. 4, 1969, discloses a process for producing phenol-aldehyde condensates, comprising heating a mixture of a phenol with an inorganic alkali catalyst, then introducing an aqueous solution of an aldehyde.

U.S. Pat. No. 3,793,201, Karn, Feb. 19, 1974, discloses a solution of oil-soluble basic magnesium salts of at least one organic acid and oil-soluble polyvalent metal salts of bridged phenols such as an alkylated phenol-formaldehyde condensation product of a sulfurized aliphatic hydrocarbon-substituted phenol.

U.S. Pat. No. 4,147,643, Pindar et al., Apr. 3, 1979, discloses additive compositions made by reacting (A) an aromatic compound having an OH or SH group, e.g. an alkyl substituted phenol; (B) an aldehyde; (C) a non-amino hydrogen, active hydrogen compound capable of forming Mannich bases (e.g., phenols); and optionally (D) an aliphatic alkylating agent. Sulfurized composition are made by sulfurizing the above compositions with elemental sulfur. The aromatic compounds of (A) can include linked poly-ring aromatic nuclei such as

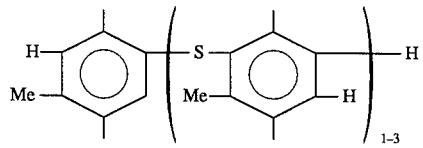

The compositions of this reference were believed to contain bridges derived from the organic residue of the aldehyde (B) linking the organic residues of the aromatic compound (A) and the active hydrogen compound (C). Thus, when (B) is formaldehyde, methylene bridges are formed. Additives such as ash-producing detergents may also be present.

U.S. Pat. No. 4,769,501, Iwahara, Sep. 6, 1988, discloses a process for producing an alkylphenol comprising reacting a phenol with an aldehyde and hydrogen in the presence of a catalyst such as an alkaline earth metal hydroxide.

SUMMARY OF THE INVENTION

The present invention provides a metal salt or boron compound of a hydrocarbyl-substituted aromatic hydroxy compound comprising at least two hydroxy-substituted aromatic rings bridged by sulfur, wherein at least one such aromatic ring bears a substituent ortho to a hydroxy group, the substituent being an α-hydroxy hydrocarbyl group or a —$C(O)R^2$ group, where $R^2$ is hydrogen or hydrocarbyl. The invention further provides lubricants, functional fluids, fuels, and concentrates comprising the foregoing salt. The invention further provides a process for producing the above composition, comprising reacting under non-condensing conditions at least one aldehyde or a reactive equivalent thereof, at least one hydrocarbyl-substituted, aromatic hydroxy compound having at least two hydroxy-substituted aromatic rings bridged by sulfur, and at least one basic metal compound or boron compound.

DETAILED DESCRIPTION OF THE INVENTION

The present invention relates to metal salts or boron compounds of certain selected aromatic hydroxy compounds, sometimes referred to as saligenins, which exhibit useful properties and overcome certain of the disadvantages that have been heretofore encountered. The salts comprise a metal ion portion and an anionic portion; the suitable metals will be first described in detail.

The metal salts or boron compounds can be based on any metal, but preferably they are salts of an alkali metal, an alkaline earth metal, or a metal from group 1b, 2b, 7b, or 8 of the transition metals, or mixtures thereof. Alkali metals include lithium, sodium, potassium, rubidium, and cesium; alkaline earth metals include magnesium, calcium, strontium, and barium. The above-mentioned transition metals include copper, silver, gold, zinc, cadmium, mercury, manganese, rhenium, iron, cobalt, nickel, ruthenium, rhodium, palladium, osmium, iridium, and platinum. Francium, radium, and technicium are formally included in the above groups but are not normally employed because of their scarcity and radioactivity. Among these, the preferred metals are magnesium, manganese, cobalt, copper, and zinc, and the most preferred metal is magnesium.

Alternatively, the material be a boron compound; such materials would not normally be categorized as "salts." Boron compounds such as boric acid can react with substituted phenolic materials to form a variety of structures such as the following:

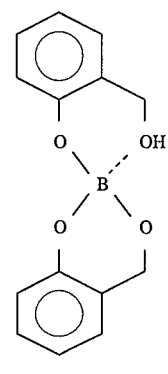

or

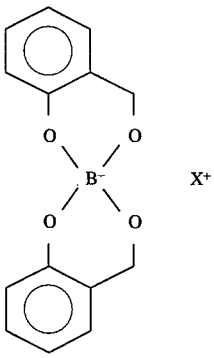

These and equivalent structures are included within the scope of the present invention.

Salts, and in particular metal salts, may be characterized as partial salts, neutral salts, or overbased salts, depending on the amount of the metal ion that is present. All such types are encompassed within the scope of the present invention. Neutral salts are those which contain approximately one equivalent of metal per each equivalent of acidic function (in this case, per each aromatic hydroxy group). The expression "approximately one equivalent" can be interpreted to mean 90–110% of the theoretical equivalent amount, preferably 95–102%, and most preferably about 100%. Overbased salts, in contrast, also referred to as superbased or hyperbased materials, are characterized by a metal content in excess (and often greatly in excess) of that which would be present according to the stoichiometry of the metal and the particular acidic organic compound reacted with the metal. The amount of excess metal in a salt is commonly expressed in terms of metal ratio. The term "metal ratio" is the ratio of the total equivalents of the metal to the equivalents of the acidic organic compound. A neutral metal salt has a metal ratio of one. A salt having 4.5 times as much metal as present in a normal salt will have metal excess of 3.5 equivalents, or a ratio of 4.5. The salts of the present invention, if overbased, can have any metal ratio in excess of 1.0, such as 1.5, preferably 3, and more preferably 7, up to 40, preferably 25, and more preferably 20.

The basicity of overbased materials generally is expressed in terms of a total base number. A total base number is the amount of acid (perchloric or hydrochloric) needed to neutralize all of the overbased material's basicity. The amount of acid is expressed as potassium hydroxide equivalents. Total base number is determined by titration of one gram of overbased material with 0.1 Normal hydrochloric acid solution using bromophenol blue as an indicator. The overbased materials of the present invention can, if desired, have a total base number of at least 20, preferably 100, and more preferably at least 200. Overbased materials generally have a total base number up to 600, preferably 500, more preferably up to 400.

Overbased materials are typically prepared by reacting an acidic material (typically an inorganic acid or lower carboxylic acid, preferably an acidic gas such as sulfur dioxide, sulfur trioxide, or, most preferably, carbon dioxide) with a mixture comprising an acidic organic compound (in this case, the aromatic hydroxy compound), a reaction medium comprising at least one inert, organic solvent (mineral oil, naphtha, toluene, xylene, etc.) for said acidic organic material, a stoichiometric excess of a metal base, and a promoter.

A promoter is a chemical employed to facilitate the incorporation of metal into the overbased compositions. The promoters are quite diverse and are well known in the art, as evidenced by numerous patents. A discussion of suitable promoters, as well as formation of overbased salts in general, is found in U.S. Pat. No. 2,777,874. Promoters include alcoholic and phenolic promoters, which are preferred. Alcoholic promoters include the alkanols of one to about twelve carbon atoms, such as methanol, ethanol, amyl alcohol, octanol, isopropanol, and mixtures of these and the like. Phenolic promoters include a variety of hydroxy-substituted benzenes and naphthalenes. Mixtures of various promoters are sometimes used. For overbasing of the phenolic materials of the present invention, small amounts of sulfonic acid salts are appropriate.

If the salt of the present invention is present as an overbased salt, the metals employed are preferably an alkali metal, an alkaline earth metal, zinc, or cadmium, or a mixture thereof. Suitable sources of metals for preparation of the overbased salts are generally metal salts (broadly defined), normally metal bases. The anionic portion of the salt can be hydroxyl or oxide, which are preferred, or carbonate, borate, nitrate, etc.

Overbased materials, as initially prepared, are generally single phase, homogeneous Newtonian systems. They can be converted, however, to colloidal disperse systems (also referred to as gelled overbased materials or "non-Newtonian" overbased materials) by homogenizing a "conversion agent" with the initial overbased material. Typical conversion agents include lower aliphatic carboxylic acids, water, aliphatic alcohols, cyloaliphatic alcohols, arylaliphatic alcohols, phenols, ketones, aldehydes, amines, boron acids, phosphorus acids, carbon dioxide, and mixtures thereof. Homogenization is achieved by vigorous agitation of the two components, preferably at the reflux temperature or a temperature slightly below the reflux temperature. This conversion process is well known to those skilled in the art and is described in greater detail in U.S. Pat. No. 3,492,231.

In addition to neutral and overbased salts, the materials of the present invention encompass incompletely neutralized salts. Since, as will be described below, the anions of the salts of the present invention will normally contain two or more aromatic hydroxy groups (i.e. phenolic groups), it is possible that less than all of those hydroxy groups in a given molecule are neutralized. Thus, for example, half salts are contemplated by the present invention, wherein one phenolic OH group is in the form of the metal salt and a second phenolic group is in the form of the unneutralized OH group. (Of course, it is recognized that in practice the neutralized and unneutralized groups may be in rapid dynamic equilibrium; any one particular group might not be meaningfully identifiable as being the "neutralized" group.)

Turning now to a description of the anionic portion of the present salts, this material can be any of a variety of hydrocarbyl-substituted aromatic hydroxy compounds comprising at least two hydroxy-substituted aromatic rings, bridged by sulfur. The hydroxy-substituted aromatic rings are preferably benzene rings, that is, mononuclear, non-fused aromatic rings. However, more complicated aromatic structures, including polynuclear aromatic materials based on, for example, the naphthalene structure or heteroatom containing aromatic materials, can be employed if desired. If an aromatic nucleus other than a benzene ring is employed, the numbers and locations of substituents (described in greater detail below) will of course need to be adjusted in a manner which should be apparent to one of skill in the art, in order to provide materials which are equivalent to and encompassed within the scope of the claimed invention.

At least one of the aromatic rings (and preferably each of the aromatic rings) bears a certain substituent in a position ortho to a hydroxy group. This substituent can be an α-hydroxyalkyl group or a —C(O)R² group, where R² is hydrogen or alkyl. Most commonly the substituent will be an α-hydroxyalkyl group, although at least small amounts of the carbonyl-containing substituents are commonly also present. Such substituents are to be considered distinct from and in addition to a hydrocarbyl substituent, at least one of which must also be present on the molecule.

In most cases the anion portion of the salt will be a negatively charged species corresponding to or derived from a structure such as that shown in the following general formula (I):

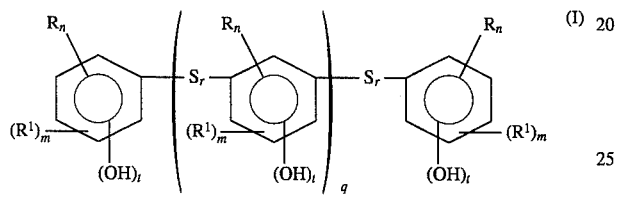

In structure (I) each R is independently a hydrocarbyl group, and n is zero or a positive integer. However, at least one ring has a hydrocarbyl group substituent, and preferably most of the aromatic rings will be so substituted. More preferably substantially all of the aromatic rings will bear a hydrocarbyl group. As used in this document, the term "hydrocarbyl" includes hydrocarbon, as well as substantially hydrocarbon groups. "Substantially hydrocarbon" describes groups which contain non-hydrocarbon substituents which do not alter the predominately hydrocarbon nature of the group.

Examples of hydrocarbyl groups include the following:

(1) hydrocarbon substituents, that is, aliphatic (e.g., alkyl or alkenyl), alicyclic (e.g., cycloalkyl, cycloalkenyl) substituents, aromatic-, aliphatic-, and alicyclic-substituted aromatic substituents and the like as well as cyclic substituents wherein the ring is completed through another portion of the molecule (that is, for example, any two indicated substituents may together form an alicyclic radical;

(2) substituted hydrocarbon substituents, that is, those substituents containing non-hydrocarbon groups which, in the context of this invention, do not alter the predominantly hydrocarbon substituent; those skilled in the art will be aware of such groups (e.g., halo (especially chloro and fluoro), hydroxy, alkoxy, mercapto, alkylmercapto, nitro, nitroso, sulfoxy, etc.);

(3) hetero substituents, that is, substituents which will, while having a predominantly hydrocarbon character within the context of this invention, contain other than carbon present in a ring or chain otherwise composed of carbon atoms. Suitable heteroatoms will be apparent to those of ordinary skill in the art and include, for example, sulfur, oxygen, nitrogen, and such substituents as, e.g. pyridyl, furyl, thienyl, imidazolyl, etc. In general, no more than about 2, preferably no more than one, non-hydrocarbon substituent will be present for every ten carbon atoms in the hydrocarbyl group. An example of such a group would be RO(CH₂CH₂O)ₙCH₂—, where n is a relatively small number and R is an alkyl group of sufficient length to impart substantial hydrocarbon character to the overall substituent. Typically, there will be no such non-hydrocarbon substituents in the hydrocarbyl group, in which case the hydrocarbyl group is purely hydrocarbon.

The hydrocarbyl groups referred to as R in the above formula is not particularly limited in its chain length, although preferably it will contain up to 50 carbon atoms, and more preferably 9 to 30 carbon atoms. A preferred hydrocarbyl is the propylene tetramer group, that is, a $C_{12}$ alkyl group derived from propylene.

The hydrocarbyl group is preferably situated on the aromatic ring in a position para to a hydroxy group.

In the formula of structure (I), each $R^1$ group is independently an α-hydroxyhydrocarbyl alkyl group or a —C(O)R² group, where $R^2$ is H (hydrogen) or hydrocarbyl. Preferably the hydrocarbyl portions of the $R^1$ groups are alkyl groups without heteroatom substitution. That is, $R^1$ is preferably an alkyl group which bears an oxygen atom (only) at the α position; the oxygen can be a hydroxy or a carbonyl oxygen, depending on the oxidation state of the α carbon atom. The number of carbon atoms in each $R^1$ group is preferably 1 or 2 to 8, more preferably 1 to 6, still more preferably 1 or 2. Most preferably $R^1$ is a formyl group or a hydroxymethyl group, thus having one carbon atom. Such groups can be derived from formaldehyde or a higher aldehyde, as is described in greater detail below.

In formula (I), each m is zero or a positive integer. However, at least one aromatic ring in the molecule has an $R^1$ substituent. Preferably each aromatic ring will contain at least one $R^1$ group; if the molecule contains three or more sulfur-bridged aromatic rings, preferably at least the outermost or terminal aromatic rings will contain an $R^1$ group. Preferably most of the $R^1$ groups will be located on their respective rings in a position ortho (adjacent) to a hydroxy group.

In formula (I), moreover, each t is 1 or 2. That is, all or substantially all of the aromatic rings are substituted by one or two hydroxyl groups. Most commonly, t will be 1 and each aromatic group can be described as a substituted phenol. It is normally anticipated that few if any of the aromatic rings of the molecule will be unsubstituted by a hydroxy group, that is, where t is 0. However, it is possible under some circumstances that a fraction of the aromatic rings in a molecule might be devoid of hydroxy substitution. While this would not be the preferred situation, such molecules would be considered to fall within the scope of the present invention. Moreover, if the hydrocarbyl group represented by R in the above formula is an aromatic hydrocarbyl group such as a phenyl group, such a group would not necessarily contain an OH group.

The total of n, m, and t on each ring will not exceed the available valences or bonding sites on the ring, taking into account the valences occupied by the sulfur linking groups. On most of the aromatic rings in Formula I, n, m, and t are each 1.

The aromatic rings in Formula I are linked by a bridging sulfur group. Simple bridged phenols and their preparation are well known. The length of the sulfur bridges is not critical, although under normal conditions the chains will normally one sulfur atom, although chains of up to 3 or even 8 carbon atoms may be formed.

The sulfur bridging groups will most commonly be attached to the aromatic rings at a position ortho to a hydroxy group. An alternative position for attachment will be the para position, but since that position will often already be occupied by a hydrocarbyl group, in most cases the sulfur bridges will be ortho. Some meta linkage is possible, but this is believed to be disfavored for kinetic or thermodynamic reasons.

The sulfur-bridged aromatic hydroxy compounds which form a part of the present salts can be prepared by known synthetic methods. The starting materials are hydrocarbyl phenols, many of which are commercially available materials, the preparation of which is well known to those skilled in the art. Hydrocarbyl phenols can be prepared, for example, by Friedel-Crafts alkylation of phenol. The hydrocarbyl phenol or phenols can be subsequently reacted with sulfur to yield a sulfur bridged material (or a mixture of sulfur-bridged materials), as shown, for instance, in the following example:

Example A. Preparation of sulfur bridged phenol.

A vessel is charged with 1000 parts (3.76 moles) of dodecylphenol (from the alkylation of phenol with polypropylene tetramer). The temperature of the mixture is raised to 54° C., and 175 parts (1.7 moles) of sulfur dichloride is added at a rate to maintain the temperature at or below 71° C. Thereafter the mixture is heated to 77°–82° C. and maintained at temperature until the acid number (to e.g. bromphenol blue indicator) is less than 4.0. The product is diluted with diluent oil.

The sulfur-bridged hydrocarbyl phenols (A), prepared as in the immediately preceding example, can then be reacted with an aldehyde or a reactive equivalent thereof (B), to form the acidic or anionic portion of the present salts.

Suitable aldehydes have the general formula RC(O)H, where R is hydrogen or a hydrocarbyl group, as described above, and include formaldehyde, acetaldehyde, propionaldehyde, butyraldehyde, isobutyraldehyde, pentanaldehyde, caproaldehyde, benzaldehyde, and higher aldehydes. Monoaldehydes are preferred. The most preferred aldehyde is formaldehyde, which can be supplied as a solution, but is more commonly used in the polymeric form, as paraformaldehyde. Paraformaldehyde may be considered a reactive equivalent of an aldehyde. Other reactive equivalents may include hydrates or cyclic trimers of aldehydes. More broadly, other synthons can be employed which can be converted to the desired groups after reaction, by methods which will be apparent to those skilled in the art. For example, imines ($R^1R^2C=N—R^3$) can be reacted to provide α-amino substituted phenols, which can be hydrolyzed to the α-hydroxy compounds. Carboxy groups can be attached to phenols and thereafter reduced to keto or hydroxy groups. Similarly nitriles can be reacted, followed by hydrolysis and/or reduction.

The reaction of the aldehyde or reactive equivalent thereof (A) with the sulfur-coupled aromatic hydroxy compound (B) is normally conducted by heating the mixture of components (A) and (B), and normally including component (C), the basic metal compound or boron compound, at a temperature of 70° to 120° C., or preferably 90° to 110° C., more preferably 90° to 100° C., for a sufficient time to effect reaction. Typical reaction times are ¼ to 4 hours, preferably ½ to 1 hour. The reaction is typically conducted in a solvent such as an aromatic solvent (toluene, xylene) for ease of handling and to aid in azeotropic removal of water, although use of a solvent is not necessary. It is also desirable, but not essential, that a small amount of aqueous base, such as 50% aqueous sodium hydroxide, be present if paraformaldehyde is the aldehyde, to catalyze smooth conversion of the paraformaldehyde to the active monomeric form. The reaction can, of course, be further modified so that the basic metal compound or boron compound (C) is subsequently combined with the reaction product of (A) and (B), thus forming the final salt in a multiple-step process.

The reaction of components (A) and (B) should be conducted under non-condensing conditions. Often an aldehyde such as formaldehyde can react with a phenol by a condensation process in which oligomeric or polymeric structures are obtained. That is, the formaldehyde addition product can further react to lead to alkylene (methylene) or oxyalkylene bridged aromatic structures:

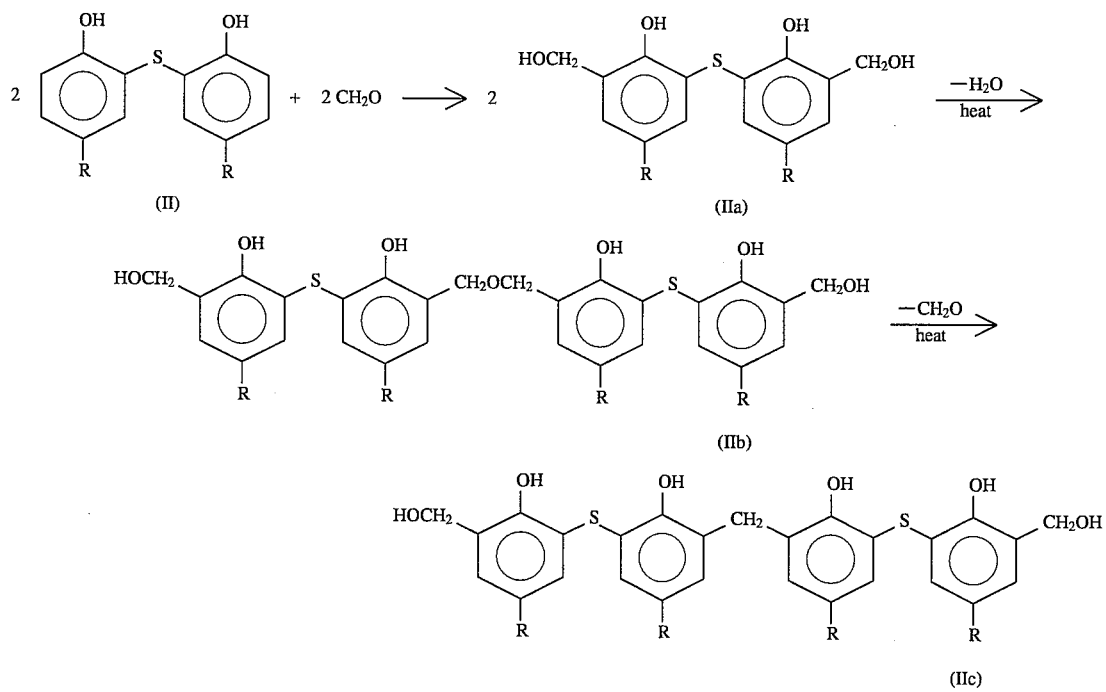

Such condensation reactions, undesirable in any substantial quantities in the present invention, are characterized by the loss of approximately ½ mole water per mole of aldehyde reacted and ultimately by formation of oligomers or polymers of alkylene (e.g., methylene) bridged aromatic rings with resulting increase in molecular weight. Condensation reactions such as these generally occur at higher reaction temperatures than are contemplated for preparing the materials of the present invention. Thus while the present non-condensed materials are preferably prepared by reaction at about 90°–100° C., materials similar to those of formula IIb might be formed upon heating at 110°–130° C. or above, while those similar to formula IIc would be formed upon further heating, i.e. at 130°–180° C. and above. Such heating has been effected in the past by a separate prolonged heat treatment step, whereby the condensation reaction is promoted. It is noted that the tendency for condensation is most apparent during the time that the aldehyde is being reacted with the phenol, and particularly before salt formation is complete. The finished salt product is generally much more stable and can be briefly heated to higher temperatures without occurrence of the undesirable condensation reactions.

The materials of the present invention are not subjected to such a subsequent heat treating step which would lead to substantial condensation reaction. Of course, it is to be expected that even at the lower temperatures which are contemplated herein, some minor amounts of condensation may unavoidably occur. Thus the description of the present materials as non-condensed, or as having been prepared under non-condensing conditions, is intended to mean that the materials are substantially non-condensed and the conditions are substantially non-condensing, such that the majority, and preferably the large majority, of the material is non-condensed. The fraction of condensed material is preferably so small as to have no significant effect on the properties of the product.

The substituted, sulfur bridged aromatic hydrocarbon component of the present invention is preferably prepared, moreover, by reaction with formaldehyde in the substantial absence of an amine capable of combining with the reactants. When phenol, formaldehyde, and an amine, particularly a secondary amine, are co-reacted, they can react by the Mannich reaction as shown:

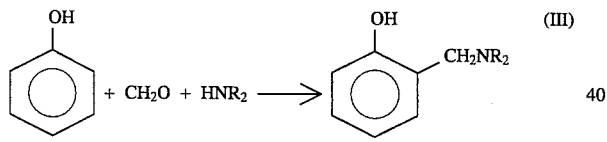
(III)

This reaction is undesirable to the extent that it precludes formation of the desired materials, that is, those which are substituted by α-hydroxyalkyl groups or —C(O)R$^2$ groups. Such products could, of course, be hydrolyzed under appropriate conditions to provide the desired products, but there would normally be little motivation for use of such an involved route.

In the above-described reactions, reaction of the aldehyde can lead to substituents which contain either carbonyl or hydroxyl groups, representing different oxidation states of the carbon atom alpha to the aromatic ring. For instance, the α-hydroxyalkyl group can undergo a redox reaction with ambient formaldehyde to yield the carbonyl substituent and methanol. This reaction is believed to be catalyzed by metals, in particular, sodium, copper, and iron. The presence of atmospheric oxygen can also be a factor influencing formation of the carbonyl. Both the hydroxyl-containing and the carbonyl-containing materials are considered suitable for the present invention.

Among the many possible structures which can be formed during the reactions described above, in addition to the materials which have already been described, are materials of the following structures:

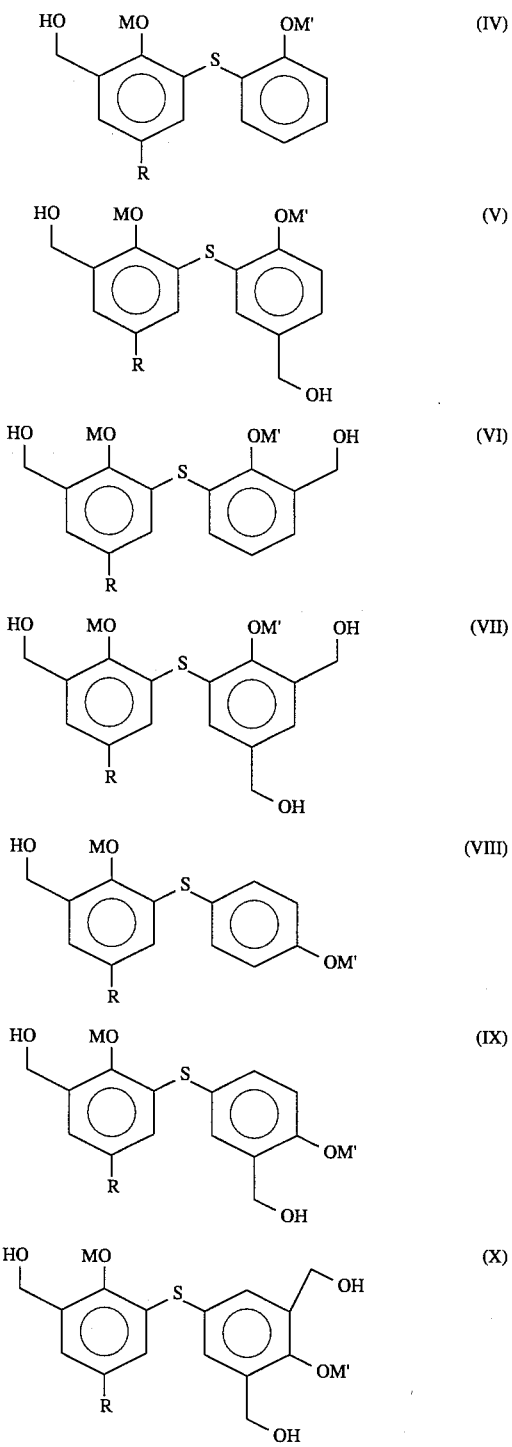

where M is a metal (ultimately acquired during the neutralization step, described below) and M' is a metal or hydrogen, and where R is a hydrocarbyl group. In addition, other related structures are possible containing more than one sulfur bridge per molecule.

The phenolic materials described above are useful for preparing metal salts, particularly metals which do not readily form salts with phenolic materials. In particular, phenolic salts of magnesium have been particularly difficult to prepare. In the past it has been difficult or impossible to prepare such salts, and particularly overbased salts, by reaction of a phenol directly with magnesium oxide or hydroxide. More difficult and circuitous routes were required, such as reaction of the acid moiety with magnesium methylate. Using the present sulfur-bridged and substituted phenolic compounds, however, the magnesium salts are readily prepared, both neutral salts having up to 90 or even 100% neutralization, and overbased salts.

The salts prepared by the process of the present invention, and in particular the magnesium salts, are useful as motor oil additives, as they have good detergent properties and can have exceptional ability to control second groove ring deposits. They can also be used as fuel additives in normally liquid fuels such as gasoline, diesel fuel, and kerosene, where they can aid in the combustion process. They can also be employed in functional fluids such as hydraulic fluids, automatic transmission fluids, where they can serve as detergents (particularly if overbased) or as extreme pressure agents. The salts will normally be used in a property-improving amount, normally 0.1 to 10 percent by weight, preferably 0.5 to 5 percent, most preferably 1.5 to 3 percent. The specific amounts will vary with the end use. The salts of the present invention can be supplied directly, or they can be supplied as a concentrate comprising the salt and a concentrate-forming amount of a normally liquid organic diluent. Typically the concentrate will comprise 10 to 90 percent of the salt, preferably 20 to 80 percent, and the balance will be the diluent, although other additives can also be present in the concentrate in suitable amounts. The identity of the diluent will be determined by the end use to which the salt will be placed. Typically, for lubrication applications, the diluent will be an oil of lubricating viscosity.

EXAMPLES

Example 1

A flask is charged with 6.1 equivalents of sulfur-coupled propylene tetramer-substituted phenol (containing diluent oil and having on average 1 S bridge per molecule), 5.5 equivalents of magnesium oxide, 0.4 equivalents of 50% aqueous sodium hydroxide, and 400 g toluene. The reaction mixture is stirred for 5 minutes. Paraformaldehyde, 7.9 equivalents, is added to the mixture and the mixture is heated to 105°–110° C. and held at temperature for 6 hours. During this time 112 mL of an aqueous phase is collected by azeotropic distillation. The resulting salt is purified by centrifugation, collecting and concentrating the resulting decantant, and filtering the mixture through DD1600 filter aid. To the filtrate (which contains the product) is added 620 g of mineral oil diluent to give a material having 38.9% total diluent oil.

Example 2

A flask is charged with 12 equivalents of the sulfur-coupled propylene tetramer-substituted phenol of Ex. 1, 10.8 equivalents of magnesium oxide, 0.63 equivalents of 50% aqueous sodium hydroxide, and 150 g toluene. The reaction mixture is stirred for 5 minutes. Paraformaldehyde, 15.6 equivalents, is added to the mixture and the mixture is heated to 110° C. under a nitrogen purge, 28 L/hr (1.0 SCFH) and held at temperature for about 3 hours, at which time 230 mL aqueous material had been collected. An additional 1000 g toluene is added and the mixture is heated for an additional 1 hour. The resulting product is purified, filtering the mixture through DD1600 filter aid and concentrating the filtrate in vacuo. The product contains 23.8% by weight diluent oil.

Example 3

A flask is charged with 1.0 equivalents of the sulfur-coupled propylene tetramer-substituted phenol of Ex. 1, 1.0 equivalents of paraformaldehyde, and 5 g (a catalytic amount) of 50% aqueous sodium hydroxide. The reaction mixture is heated to 100° C. and held at temperature for 2 hours, at which time is added 2.0 equivalents (excess) boric acid ($H_3BO_3$) and 100 g toluene. The mixture is heated to reflux, and about 24 mL of an aqueous phase is collected. The temperature is raised to 150° C. and maintained at temperature for about 5 hours, during which time an additional 16 mL aqueous phase material is collected. The mixture is cooled and 300 g toluene and 50 g diluent oil are added. The solution is filtered over a filter aid and the filtrate is concentrated in vacuo. The product contains 32% diluent oil.

Example 4

A flask is charged with 2.78 equivalents of sulfur-coupled propylene tetramer-substituted phenol (on average 3 S bridges and 4 aromatic rings per molecule), 2.78 equivalents of zinc oxide, 15 g (a catalytic amount) of 50% aqueous sodium hydroxide, 2.78 equivalents of paraformaldehyde, and 500 g toluene. The mixture is heated, with stirring, to 100°–105° C. and held at temperature for about 3 hours. During this time 50 mL of an aqueous phase is collected by azeotropic distillation. The resulting salt is purified by vacuum stripping (120° C., 1.3–4.0 kPa (10–30 mm Hg)) and filtering through filter aid. The product contains 39% diluent oil.

Example 5

A flask is charged with 1.0 equivalent of the sulfur-coupled propylene tetramer-substituted phenol of Ex. 1, 1.0 equivalents of manganese carbonate, 4 g (a catalytic amount) of 50% aqueous sodium hydroxide, 125 g toluene, and 1.1 equivalents of paraformaldehyde. The reaction mixture is heated, with stirring, to reflux for 3 hours and then to 100° C. for 3 hours. The product is collected by filtration (over filter aid) and concentration in vacuo. The product contains 23.5% diluent oil.

Example 6

A flask is charged with 1.17 equivalent of the sulfur-coupled propylene tetramer-substituted phenol of Ex. 1, 1.17 equivalents of $CuCO_3.Cu(OH)_2$, 1 g (a catalytic amount) of 50% aqueous sodium hydroxide, 100 g toluene, and 1.17 equivalents of paraformaldehyde. The reaction mixture is heated, with stirring, at 80°–90° C. for 2.5 hours, collecting 23 mL aqueous material. The mixture is cooled to 60° C. and 100 g of naphtha is added. The mixture is centrifuged and the supernatant concentrated in vacuo. The product contains 23% diluent oil.

Example 7

A flask is charged with 0.5 equivalents (480 g) of the sulfur-coupled propylene tetramer-substituted phenol of Example 4, 0.5 equivalents (15 g) paraformaldehyde, 3 g 50% aqueous sodium hydroxide, 0.5 equivalents (23 g) cobaltous hydroxide, and 75 g toluene. The mixture is heated to reflux and maintained at temperature for 4 hours. Sixteen mL of aqueous material is removed by azeotropic distillation. The temperature is raised to 150° C.; thereafter the mixture is cooled and about 300 mL toluene is added. The mixture is filtered over a filter aid, the filtrate collected, and concentrated by heating at 100° C. under 1.3–4 kPa (10–30 mm Hg). The product contains 39.5% diluent oil.

Example 8

A flask is charged with 0.54 equivalents (300 g) of the reaction product of the sulfur-coupled propylene tetramer-substituted phenol of Ex. 1 with formaldehyde (1:1 mole ratio), 1.0 equivalents (59.5 g) of cobalt carbonate, $CoCO_3$, and 200 g toluene. The reaction mixture is heated, to 110° C. for 1.5 hours. 10 mL water is added, and the mixture is refluxed for 3 hours, collecting 14 mL aqueous material. The mixture is filtered and the filtrate is concentrated in vacuo. The product contains 23.4% diluent oil.

Example 9

A flask is charged with 1.0 equivalents (960 g) of the sulfur-coupled propylene tetramer-substituted phenol of Example 4 and 500 g toluene. The mixture is stirred and 5 g 50% aqueous sodium hydroxide, 39 g paraformaldehyde, and 21 g magnesium oxide are added. The mixture is heated to 110° C. and maintained at that temperature for 1 hour, cooled down, and held again at 110° C. for 6 hours on the next day. Thirteen mL of aqueous phase is collected by azeotropic distillation. The mixture is vacuum stripped to remove volatiles, and the residue filtered through filter aid. The product contains 40.2% diluent oil.

Example 10

A flask is charged with 1000 g (2.57 equivalents) of the sulfur-coupled propylene tetramer-substituted phenol of Example 1, 400 g diluent oil, 200 g toluene, and 10 g 50% aqueous sodium hydroxide. The mixture is stirred and 95 g calcium hydroxide (2.57 equivalents) and 88 g paraformaldehyde (2.96 equivalents) are added. The mixture is heated to 110° C. and maintained at temperature for 6 hours. Forty-two mL of an aqueous phase is removed by azeotropic distillation. The mixture is cooled, filtered through a filter aid, and concentrated in vacuo. The product contains 43.5% diluent oil.

Example 11

A flask is charged with 389 g (1.0 equivalents) of the sulfur-coupled propylene tetramer-substituted phenol of Example 1, 30 g (1.0 equivalents) of paraformaldehyde, 2 g 50% aqueous sodium hydroxide, 200 g toluene, and 37 g calcium hydroxide. The mixture is heated with to reflux and maintained at temperature for 5 hours. Twenty-five mL of an aqueous phase is removed by azeotropic distillation. The heating is discontinued and 185 g diluent oil, 100 g toluene, 150 g methanol, 100 g mixed alcohols (iso-amyl and butyl alcohols), and 148 g additional calcium hydroxide are added. The mixture is heated to 50° C. and a carbon dioxide sparge (2.5 equivalents/hr) is begun. After 2 hours the mixture is heated to remove the volatiles. The resulting viscous mixture is diluted with toluene, centrifuged, and concentrated in vacuo. The product contains 34.1% diluent oil.

Example 12

A flask is charged with 668 g (1 equivalent) of the product of Example 1, 27 g (0.05 equivalent) of a primary, branched-chain alkyl (number average m.w. about 500) benzenesulfonic acid composition (which includes about 12% diluent oil), 100 g diluent oil, 40 g methanol, 30 g water, 800 g toluene, and 42 g (2 equivalents) magnesium oxide. The mixture is heated with stirring to 42° C. Carbon dioxide is bubbled through the mixture at 28 L/hr (1 SCFH, 2.5 equivalents/hr). After 45 minutes, an additional charge of 42 g magnesium oxide is added, and the $CO_2$ sparge is continued for an additional 45 minutes. Thereafter the temperature of the mixture is increased gradually to 130° C., removing water, methanol, and toluene with a nitrogen sparge. The resulting mixture is cooled and filtered over a filter aid, to isolate the overbased material. The product contains 42.6% diluent oil.

Examples 13–18

The materials from certain of the above Examples are formulated in an Exxon 10W-40 basestock oil, along with traditional additives, to prepare a material for testing as an engine lubricant. The additives in each case comprise one or more conventional dispersants, in an amount of about 6–8.5% by weight based on the composition; one or more detergents (overbased materials), in an amount of about 1.4 to about 2.4% by weight, at least one extreme pressure agent, in an amount of about 0.75 to about 1.5% by weight, and, in some cases, a rust preventative in an amount of about 0.1% by weight. The dispersants are about 55% active chemical and 45% diluent oil; the detergents are about 50% active chemical and 50% diluent oil; the extreme pressure agents are about 90% active chemical and 10% diluent oil, and the rust preventative is about 100% active chemical. Since the detailed formulations of the compositions vary, precise comparisons cannot be made between compositions.

The compositions are subjected to a series of engine tests, including the Caterpillar 1G2 test, the Sequence IIE and Sequence IID tests, and the L-38 bearing corrosion test. Each of these are well-known tests described in SAE documentation (Society of Automotive Engineers). It is understood by those skilled in the art that engine testing is subject to a certain amount of variability; hence the individual result, whether good or bad, from any single test is of less importance than the preponderance of all of the test results. The results are presented in Table I.

TABLE I

| | Ex. 13 | Ex. 14 | Ex. 15 | Ex. 16 | Ex. 17 | Ex. 18 |
|---|---|---|---|---|---|---|
| Mat'l from Ex.[a] | 2 | 10 | 10 | 9 | 9 | 4 |
| Am't (%) | 2.17 | 2.75 | 2.25 | 2.39 | 1.82 | 2.28 |
| % Active saligenin | 1.65 | 1.55 | 1.27 | 1.42 | 1.08 | 1.39 |
| Rust Additive | + | − | + | + | − | + |
| 1G2: hours | 240, 240[b] | 480 | 240 | 240 | | 120 |
| WTD | 126, 255 | 274 | 208 | 264 | | 190 |
| TGF, % | 67, 63 | 62 | 77 | 65 | | 78 |
| IIE: | | | | | | |
| AES | 9.56 | | | 9.22 | | |
| APV | 8.68 | | | 9.07 | | |
| RLD | 5.9 | | | 3.83 | | |
| Wear: | | | | | | |
| max. | 4 | | | 8 | | |
| avg. | 2 | | | 5.6 | | |
| Visc. incr. | 219 | | | 334 | | |
| IID: AER | | | | | 8.54 | |
| L-38: BWL(mg) | | | | | 40 | |
| PV | | | | | 9.6 | |

[a] One experiment using 2.59% of the material from Example 1 (1.59% of saligenin) gave a WTD of 354 after 240 hours.
[b] Duplicate runs.

TABLE I-continued

|  | Ex. 13 | Ex. 14 | Ex. 15 | Ex. 16 | Ex. 17 | Ex. 18 |
|---|---|---|---|---|---|---|

Notes:
WTD = weighted total demerits
TGF = top groove fill
AES = average engine sludge
APV = average piston varnish
RLD = ring land deposit
AER = average engine rust
BWL = bowl
PV = piston varnish
[blank] = test not run Each of the documents referred to above is incorporated herein by reference. Except in the Examples, or where otherwise explicitly indicated, all numerical quantities in this description specifying amounts of materials, reaction conditions, molecular weights, number of carbon atoms, and the like, are to be understood as modified by the word "about." Unless otherwise indicated, each chemical or composition referred to herein should be interpreted as being a commercial grade material which may contain the isomers, by-products, derivatives, and other such materials which are normally understood to be present in the commercial grade. However, the amount of each chemical component is presented exclusive of any solvent or diluent oil which may be customarily present in the commercial material, unless otherwise indicated. As used herein, the expression "consisting essentially of" permits the inclusion of substances which do not materially affect the basic and novel characteristics of the composition under consideration.

What is claimed is:

1. A composition comprising a metal salt or boron compound of a hydrocarbyl-substituted aromatic hydroxy compound which comprises at least two hydroxy-substituted aromatic rings bridged by sulfur, wherein at least one such aromatic ring bears a substituent ortho to a hydroxy group, the substituent being an α-hydroxy aliphatic hydrocarbyl group or a —C(O)R² group, where R² is hydrogen or aliphatic hydrocarbyl.

2. The composition of claim 1 wherein the metal salt or boron compound is a salt of an alkali metal, an alkaline earth metal, a group 1b, 2b, 7b, or 8 transition metal, or a mixture thereof.

3. The composition of claim 2 wherein the salt is magnesium, manganese, cobalt, copper, or zinc salt.

4. The composition of claim 3 wherein the salt is a magnesium salt.

5. The composition of claim 1 wherein the metal salt or boron compound is a boron compound.

6. The composition of claim 1 wherein the metal salt or boron compound is a salt containing about 1 equivalent of metal per each equivalent of phenolic OH.

7. The composition of claim 1 wherein the metal salt or boron compound is an overbased metal salt.

8. The composition of claim 1 wherein the hydrocarbyl-substituted aromatic hydroxy compound has the structure

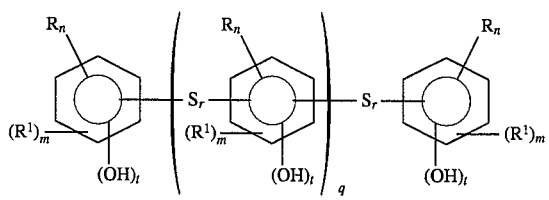

wherein each R is independently hydrocarbyl; each $R^1$ is independently α-hydroxy aliphatic hydrocarbyl or —C(O)R² where R² is H or aliphatic hydrocarbyl; each n and m is zero or a positive integer and each t is 1 or 2, provided that at least one aromatic ring has an R substituent and at least one aromatic ring has an $R^1$ substituent, and that for each aromatic ring the sum n+m+t is less than or equal to the number of available valences on the ring; q is zero or a positive integer; and each r is 1 to about 8; provided that at least one $R^1$ group is ortho to an —OH group.

9. The composition of claim 8 wherein each hydrocarbyl group R independently contains 1 to about 50 carbon atoms.

10. The composition of claim 9 wherein each hydrocarbyl group R contains about 9 to about 30 carbon atoms.

11. The composition of claim 8 wherein each aromatic ring has at least one hydrocarbyl group R.

12. The composition of claim 8 wherein on most aromatic rings the hydrocarbyl group R is present and is para to the hydroxy group.

13. The composition of claim 8 wherein each $R^1$ group contains up to 6 carbon atoms.

14. The composition of claim 8 wherein each $R^1$ group is hydroxymethyl or formyl.

15. The composition of claim 14 wherein each $R^1$ group is hydroxymethyl.

16. The composition of claim 8 wherein on most aromatic rings a bridging sulfur is ortho to a hydroxy group.

17. The composition of claim 8 wherein on most aromatic rings n, m, and t are each 1.

18. The composition of claim 8 wherein q is 0, 1, or 2.

19. The composition of claim 17 wherein each r is 1 to 3.

20. A process for producing the composition of claim 1, comprising reacting under non-condensing conditions:

(A) at least one aldehyde or reactive equivalent thereof, (B) at least one hydrocarbyl-substituted, aromatic hydroxy compound having at least two hydroxy-substituted aromatic rings bridged by sulfur, and (C) at least one basic metal compound or boron compound.

21. The process of claim 20 wherein the reaction is conducted by heating a mixture of components of (A), (B), and (C) at a temperature of about 70° to about 120° C.

22. The process of claim 21 wherein the mixture is heated at a temperature of about 90° to about 110° C.

23. The process of claim 20 wherein (C) is an oxide, hydroxide, or carbonate of an alkali metal, an alkaline earth metal, a group 1b, 2b, 7b, or 8 transition metal, or a mixture thereof.

24. The process of claim 20 wherein (C) is an oxide, hydroxide, or carbonate of magnesium, manganese, cobalt, copper, or zinc.

25. The process of claim 20 wherein (C) is magnesium oxide or magnesium hydroxide.

26. The process of claim 19 wherein the aldehyde or reactive equivalent thereof is formaldehyde or paraformaldehyde.

27. The product of the process of claim 20.

28. A lubricant or functional fluid comprising a major amount of an oil of lubricating viscosity and a property-improving amount of the composition of claim 1.

29. A concentrate comprising about 10 to about 90 percent by weight of the composition of claim 1 and a normally liquid organic diluent.

* * * * *